United States Patent [19]
Valette

[11] Patent Number: 5,394,239
[45] Date of Patent: Feb. 28, 1995

[54] SPINAL SENSOR WITH INTEGRATED OPTICS TO DETECT CHEMICAL SUBSTANCES

[75] Inventor: Serge Valette, Grenoble, France

[73] Assignee: Commissariat A l'Energie Atomique, France

[21] Appl. No.: 99,221

[22] Filed: Jul. 29, 1993

[30] Foreign Application Priority Data

Aug. 10, 1992 [FR] France .................. 92 09869

[51] Int. Cl.6 .............................. G01B 9/02
[52] U.S. Cl. .................. 356/345; 356/361; 356/128
[58] Field of Search ........... 356/345, 361, 128, 133; 385/12, 14; 250/227.27, 227.19

[56] References Cited

U.S. PATENT DOCUMENTS 5,289,256  2/1994  Gramling ................. 356/345

FOREIGN PATENT DOCUMENTS 0061884   6/1982  European Pat. Off. .
0218021  10/1985  Japan ...................... 356/350
2228082   8/1990  United Kingdom .
9205329   4/1992  WIPO .

OTHER PUBLICATIONS

Appl. Phys. Lett. 55(23) 4 Dec. 1989, "Efficient Coupling of a Semi Conductor Laser to an Optical Fiber by Means of a Tapered Waveguide on Silicon".

Primary Examiner—Samuel A. Turner
Attorney, Agent, or Firm—Pearne, Gordon, McCoy & Granger

[57] ABSTRACT

The invention concerns a sensor with integrated optics, to detect chemical substances, including a double spiral interlaced with wave guides and integrated on a substrate (13) receiving the signal of a light source (14) through a first optical component (15) able to separate into two portions the light intensity emitted by the source and sending output signals onto at least one detector (17) through a second optical component (16), the first of the two guides (11) being a reference guide isolated from the influence of the substance to be measured, and the second (12) being a measuring guide affected by the substance to be measured.

14 Claims, 6 Drawing Sheets

SPINAL SENSOR WITH INTEGRATED OPTICS TO DETECT CHEMICAL SUBSTANCES

FIELD OF THE INVENTION

The present invention concerns a sensor with integrated optics for the detection of chemical substances.

BACKGROUND OF THE INVENTION

So as to detect the presence of chemical substances, it is possible to use optical sensors implementing two types of phenomena:
 a refraction index modification,
 a light absorption modification.

These modifications may either directly concern the substance to be measured (gas or liquid) or make use of a relay material which selectively adsorbs or absorbs the substance to be measured which modifies its optical characteristics.

Unfortunately, most of the time, these modifications are extremely slight but may be compensated in optics by a large length of interaction. In fact, the index variation induced by the substance to be measured $\Delta n$ produces a phase variation $\Delta\phi = 2\pi/\Delta$ nL. If the minimum phase variation able to be detected in an interferometric diagram is $\delta\phi$, the minimum detectable variation $\delta n$ is $\delta n = \lambda \delta\phi/2\pi$ L. If L is extremely large, $\delta n$ may be extremely small.

Similarly, the absorption $\Delta\alpha$ directly influences the outgoing luminous intensity signal Is. If the minimum detectable relative variation is $\delta I/Is$, (Is being the luminous intensity of the undisturbed system), the latter is proportional to $\Delta\alpha L$. The minimum detectable absorption variation is thus conversely proportional to L.

A French patent application FR-A-88 14433 filed on 4 November 1988 describes an integrated optical device used to measure the refraction index of a fluid including (a) a light guide of an effective index n1 of the guided mode formed on a substrate and comprising a guiding film intended to carry luminous beams and inserted between one lower film and one upper film having refraction indices smaller than that of the guiding film, (b) a zone for measuring the interaction of the light guide intended to be in contact with the fluid, the upper film at the level of the measuring zone having a thickness smaller than the penetration distance of the dying out wave of the guided luminous beam and, outside this interaction zone, a thickness larger than said penetration distance of this same dying out wave and formed, at least partly, in the light guide and comprising one optical reference circuit and one optical measuring circuit including the measuring zone so as to measure the phase jump introduced by a change of effective index n2 of the guided mode due to the fluid.

This device makes use of the fact that, in integrated optics, the effective index of a guided mode depends on all the parameters of the structure of the guide and in particular the thickness of the refraction indices of the various films constituting this guide. Also, the modification of one of these parameters, and in particular the refraction index of one of these films, modifies the effective index of the guided mode in question and thus locally introduces a phase modification of the light which may be detected by means of interferometry.

In conventional known types of optical devices, the need to implement a large length of interaction also results in having a large spatial requirement. In guided optics, these two constraints may be reconciled by the use of optical fibers.

However, it is then extremely difficult to have a reference independent of the step carried out concerning disturbances caused by various parasitic effects, for example due to temperature or pressure variations or variations of the incoming light intensity.

The aim of the invention is to have a wave guide structure able to avoid these effects where it is desired to detect the presence of a fluid, gas or liquid, such as a concentration of methane lower than the explosivity limit (1%), and also detect the modification of the concentration of a solute in a liquid, for example pH time variations or an antigene-antibodies concentration variation in biomedical applications.

SUMMARY OF THE INVENTION

The present invention concerns a sensor with integrated optics, especially for chemical substances, wherein it includes a double spiral interlaced with wave guides integrated on a substrate and receiving the signal from a light source through a first optical component able to separate into two portions the light intensity emitted by the source and sending these outgoing signals onto at least one detector through a second optical component, and wherein the first of the two guides is a reference guide isolated from the influence of the substance to be measured, the second being a measuring guide affected by the substance to be measured.

Advantageously, the inlets and outlets of the spiral are situated on the same side of the substrate, this embodiment making it possible to obtain a more compact structure more practical in use.

Advantageously, the second guide is affected by the substance to be measured, either directly or by means of a relay material. The sensor of the invention may be used to embody:
 either a direct intensity measurement (selective absorption measurement),
 or an interferometric measurement (real index measurement) with or without any simultaneous absorption measurement.

Advantageously, on one first variant, the second optical component is a bicoupler or preferably a tricoupler able to have the output signals of the guides interfered so as to measure the phase variations induced between the first reference guide and the second measuring guide, this tricoupler including a central guide associated with the measuring and reference guides and disposed between said guides.

Advantageously, in one second variant, the second optical component is able to connect the two guides and two detectors so as to detect the outgoing luminous intensities of these guides.

Advantageously, in the inlet and outlet portions of the spiral, the two guides have a structure identical to that of the reference guide. Outside these portions, the measuring guide has a different structure allowing for measurement. The links between the inlet and outlet portions of the guide and the central measuring portion are advantageously formed by an adiabatic transition.

Advantageously, the crossing of the guides of the spiral by one of the two extremities of the latter is embodied in integrated optics via the direct crossing of the guides inside the plane of the spiral itself, the crossing angles of the various guides preferably being greater than 10 degrees.

Advantageously, the luminous wave guides are embodied in one of the Si/SiO2/Si3N4/SiO2 and Si/SiO2/SiO2 high index/SiO2 structures.

The interest of this spiral structure resides in the fact that in a reduced volume, this significantly increases the sensitivity of the sensor by acting on the number of spires.

Moreover, the fact of using two guides close to each other in an interlaced spiral makes it possible to obtain two guides having similar reactions to a parasitic environment.

DETAILED DESCRIPTION OF THE PREFERRED EMBODIMENTS

Figure 1:
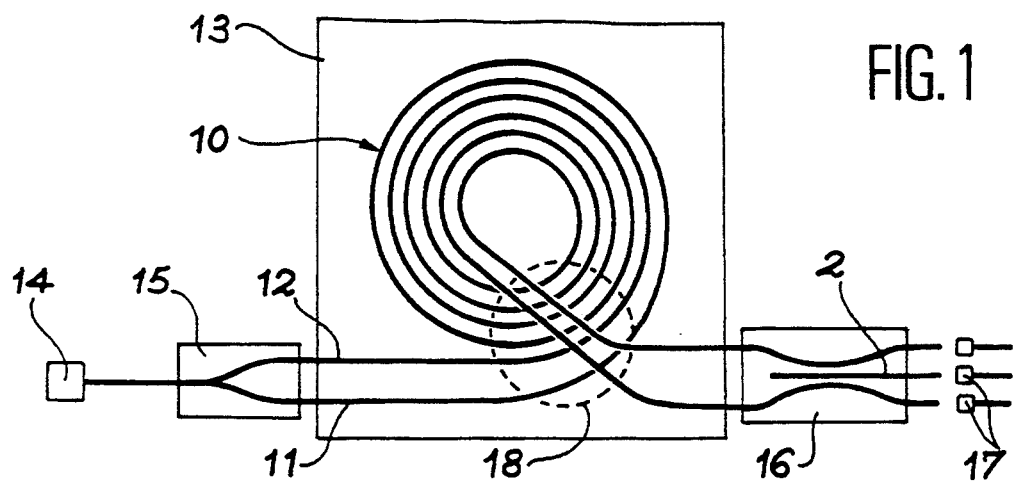
FIGS. 1 and 2 illustrate two variants of the device of the invention.
Figure 2:
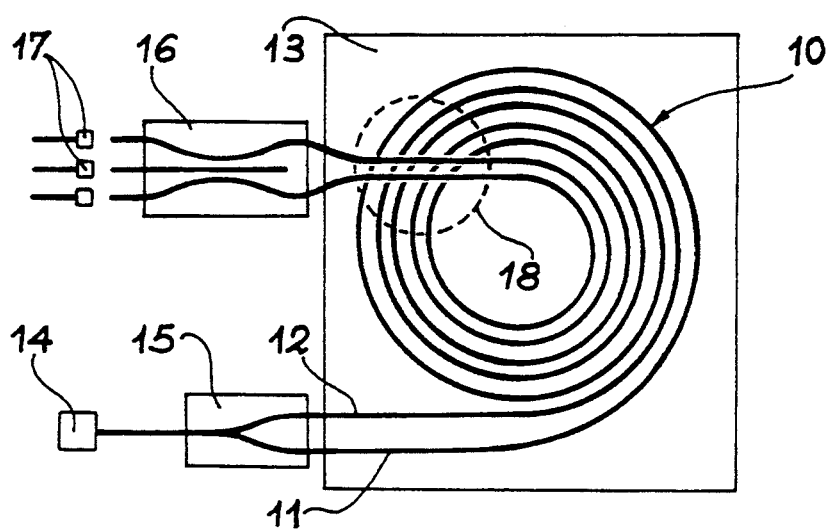

As shown on FIGS. 1 and 2, the sensor of the invention includes a double spiral 10 interlaced with wave guides 11 and 12 and integrated on a substrate 13.

This double spiral 10 receives the signal from a light source 14 through a first optical component 15 which may be a bicoupler or a Y junction, thus making it possible to separate the luminous intensity emitted by the source 14 into two equal portions.

At the outlet of the double spiral 10, the outgoing signals of the two guides 11 and 12, recombined by a second optical component 16, are sent onto one or several detectors 17.

The components 15 and 16 are advantageously embodied integrated on the same substrate as for the double spiral 10.

The crossing 18 of the guides 11 and 12 is effected by means of junctions X whose angle of crossing is preferably greater than 10 degrees so as to avoid one portion of the light, when the angle is extremely narrow, is able to be misplaced in an undesired direction and thus provoke possible harmful radio interference for exploiting results by the detector(s).

The embodiment of FIG. 2, in which the inlets and outlets of the spiral 10 are situated on the same side of the substrate 13, makes it possible to obtain a more practical compact structure. Thus, as regards biomedical applications, if disposable sensors are used, the connecting and disconnecting of connectors to the inlets and outlets of the spiral 10 is rendered much easier.

In the double spiral shown on FIGS. 1 and 2, the first guide 11 is a reference guide which is completely isolated from the influence of the substance to be measured. The second guide 12 is affected by the substance to be measured either directly or by means of a relay material. This second guide 12 is thus the sensitive element of the sensor.

The sensor of the invention may be used in two types of measurements:

A. To detect the variations of the real portion of the effective index of the guided mode mainly induced by a modification of the real refraction index afforded by the substance to be detected or by that of the relay material.

In this case, the phase variations produced between the first reference guide 11 and the second measuring guide 12 are measured. Thus, it is necessary to interfere with the outgoing signals of the guides 11 and 12. The component 16 is then a bicoupler or preferably a tricoupler.

As shown on FIGS. 1 and 2, this tricoupler 16 or three-channel coupler comprises a central guide 2 coupled to the guides 11 and 12 and disposed between said guides.

In the coupling zone, the guides 11 and 12 are adjacent to the guide 2 and the distance separating the guide 2 respectively from the guides 11 and 12 is between 1 and 10 $\mu$m and preferably between 1 and 5 $\mu$m.

For an identical partition of the light intensity, a coupling zone of typically between 1 and 15 mm is used firstly between the guide 2 and the guide 11 and secondly between the guide 2 and the guide 12.

At the level of the detection face corresponding to the outlet of the guides 11, 2 and 12, said guides are spaced well away from one another by a distance of at least more than 10 $\mu$m and typically of between about 20 $\mu$m and 50 $\mu$m so as to avoid any coupling.

The guide 2 is embodied at the same time and in the same way as for the guides 11 and 12.

Associated with this three-channel coupler 16 are three detectors 17 respectively disposed opposite the outlets of the guides 11, 2 and 12.

These detectors 17 produce an electric signal with respectively an intensity Ia, Ib and Ic representative of the interference signal formed downstream of the detection face and satisfying the following equations:

$$IA = A + B \cos \Psi + C \sin \Psi$$

$$Ib = 1 - (Ia + Ic)$$

$$Ic = A + B \cos \Psi - C \sin \Psi$$

In these equations, A, B and C are light sharing coefficients which depend on the geometry of the coupler and $\Psi$, the phase shift between the measuring beam and the reference beam.

In carrying out Ia−Ic, 2C sin $\Psi$ is obtained, whereas Ia+Ic gives 2A+2B cos $\Psi$ and Ib=1 (2A+2B cos $\Psi$).

Thus, two systems of phase quadrature fringes are obtained (phase shift of $\pi/2$) by virtue of the properties of the three-channel coupler.

In this structure, Ia+Ic and Ia−Ic are still out-of-phase by $\pi/2$, whereas in the devices with Young holes, the phase shift is $\pi/2 \pm \delta\phi$ according to technological errors and is less than 10% in most cases.

B. For detecting absorption variations:

In this case, there is no need to interfere the guides 11 and 12 and is merely sufficient to detect the luminous intensities Is1 and Is2 at the outlet of these two guides. The component 16 makes is possible to connect the guides 11 and 12 to two detectors 17.

In the two cases referred to above (A and B), the interlacing of the two guides 11 and 12 shall ensure an influence of the external parasitic parameters which is as identical as possible concerning each of them. Only the influence of the parameter to be measured shall result in a different evolution of the outgoing intensities.

The second guide may be embodied is several ways and allow for:

1. A direct contact of the guided wave and the substance to be measured (generally via the dying out wave):

For gases with indices extremely close to that of air, this method can be used. It has the drawback of not being selective if several gases are present at the same time and if the induced phase variations (interferometric measurement) are measured.

This method may become selective if the absorption variations are measured, provided an effective wavelength is used which corresponds to an absorption line particular to the gas to be measured. Certainly, it is necessary to ensure that the reference guide is transparent for this wavelength and that a source is available able to generate it.

In all these cases, the isolation film of this guide 12 is partially or completely suppressed and interaction is used between the dying out waves of the guided mode and the environment medium.

2. An indirect contact of the guided wave and the substance to be measured:

Contact then takes place by means of a dielectric material transparent and sensitive to the effective wavelength, that is able to absorb or adsorb the gas (or possibly the liquid) to be measured. This absorption or adsorption modifies either the index of the sensitive dielectric material or its absorption or the both of them.

These modifications are expressed by a modification of the phase or absorption (or both) of the guided wave. The dielectric material thus needs to be placed in such a way that the guided wave can be in contact with it.

The two guides 11 and 12 of the spiral 10 may be embodied with the following structures:

OIS1: Si/SiO2/Si3N4/SiO2 or

OIS2: Si/SiO2/SiO2 high index/SiO2

Figures 3, 4:
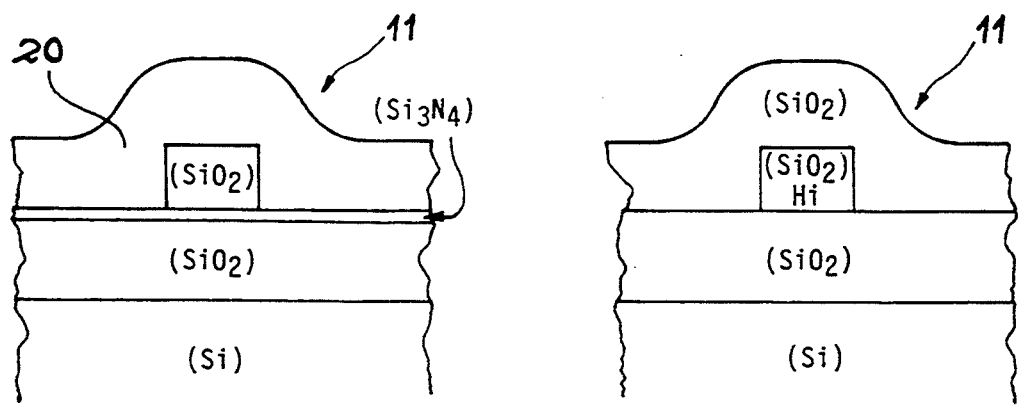
FIGS. 3 to 16f illustrate various embodiments of the guides forming the spiral of the sensor of the invention.

So as to embody the first guide 11 of the sensor of the invention isolated from the influence of the substance to be measured, this isolation of the OIS1 and OIS2 type guides is relatively simple:

for a guide 11 of the OIS1 type as shown on FIG. 3, the dielectric or nonconductor 20 placed on the guide is selected so as to isolate the guide defined by the silica block on silicon nitride. It needs to have:

an index no<nSiO2, a thickness being such that the dying out wave associated with the guided mode cannot see the environment, good impermeability with respect to external agents and certainly in particular to the substance to be detected.

This nonconductor 20 may thus differ according to the substance to be detected. In practice, suitably annealed silica gels or optical glues are able to ensure this isolation.

For an OIS2 type guide 11 as shown on FIG. 4, the covering of such a structure ensures its isolation with regard to the outer medium if the upper silica film SiO2 is sufficiently thick, that is greater than the penetration of dying out waves associated with the guided mode.

Figure 5:
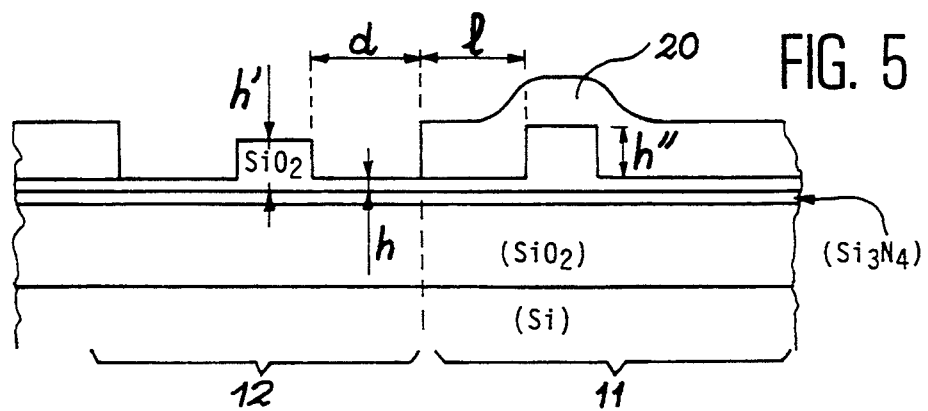

So as to embody the second guide 12 of the sensor of the invention and affected by the substance to be measured, several configurations are possible:

1. By direct contact of the guided wave and the substance to be measured:

for an OIS1 type guide 12 as shown on the left portion of FIG. 5, the width d on both sides of the measuring guide defined by the silica block SiO2 needs to be calculated so as to avoid any coupling between the block of the guide 12 and the adjacent planetary portion possibly surmounted by a nonconductor. In practice, the distance d is greater than or equal to a value of about several microns.

This FIG. 5, like FIGS. 6 to 14, is a cross section of two adjacent guides 11 and 12 of the spiral 10, the measuring guide 12 being shown in the left-hand portion of the figure.

Secondly, it is essential that the dying out wave of the guided mode "sees" the fluid to be measured and thus that the height h or h' is less than the penetration depth p of this dying out wave in the upper silica film.

Of course, h<h' exists to ensure the lateral confinement of the guided mode.

if h'>p, h<p, contact is made solely via the sides and not via the top of the guide, if h'<p=>h<p, contact is made via the sides and the top. Sensitivity may be better for a given spiral length 10, h able to be nil in both cases.

In this embodiment of FIG. 5, with two neighbouring guides 11 and 12 of the spiral cross section, the distance l is calculated so that the protection of the reference guide 11 is total. The distance d is such that any coupling between the measuring and reference guides is prohibited.

Figure 6:
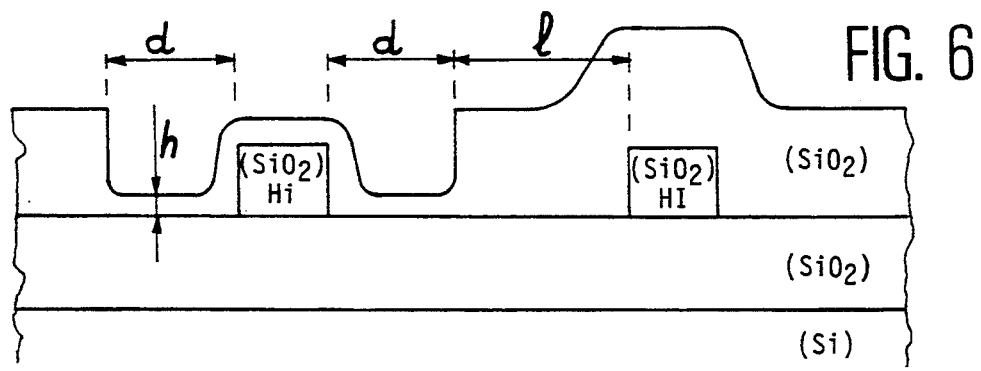

The thickness h" of the silica SiO2 of the reference guide 11 is generally greater than p (penetration depth of the dying out wave), h" thus possibly being different from h'.

for an OIS2 type guide 12 as shown on the left part of FIG. 6, the silica covering film SiO2 has a thickness h<p and possibly nil, "SiO2 HI" signifying a high index SiO2. Contact then takes place via the sides and the top of the guide.

Intermediate configurations may be embodied.

In this representation of FIG. 6, the distance d is calculated so that any coupling between the two reference and measuring guides is impossible.

The distance l is calculated so that the reference guide is completely isolated from the environment.

The height h is sufficiently small so as to ensure interaction between the guided wave and the surrounding medium to be analysed; h may be nil.

2. For an indirect contact of the guided wave and the substance to be measured, the following configurations are then able to be embodied:

a) if the real index of the sensitive nonconductor nDS is less than the index of the SiO2 nSiO2: nDS<nSiO2.

This is the case for a large number of polymers: for example, ether lauryl polyoxyethylene ("POELE") has already been used (for detecting methane (C2H4)) in quite different sensor configurations: its index nDS is slightly smaller than that of the silica SiO2: (nDS~1.4512).

Figure 7:
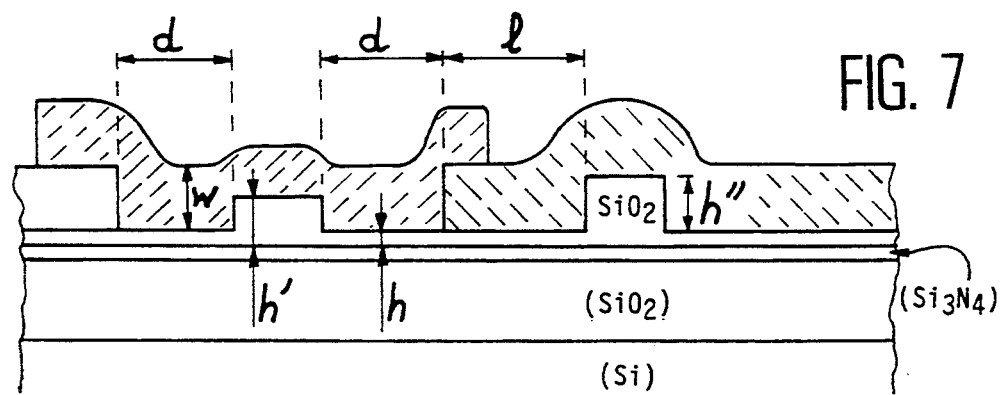

For an OIS1 type guide as shown on the left part of FIG. 7, the thickness w of the sensitive nonconductor may be any, provided the absorbtion of the fluid is able to reach the zone for interacting with the guided wave.

In practice, w is between one fraction of a micrometer and several micrometers.

The conditions concerning the heights h and h' and the distances l and d are identical to those previously given in the case of a direct contact of the guided wave and the substance to be measured.

Figure 8:
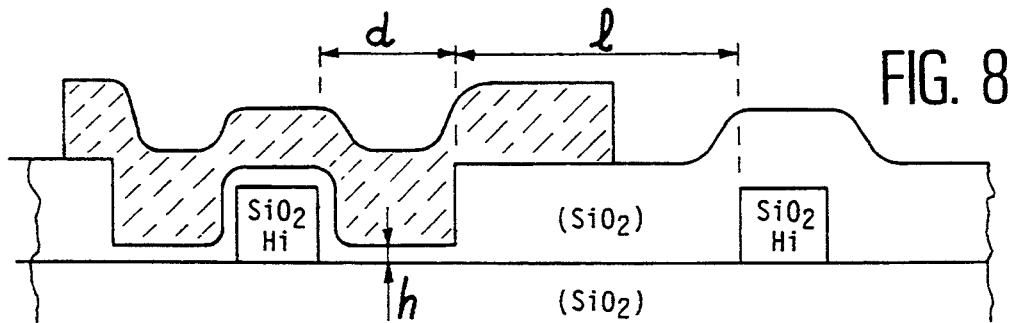

In an OIS2 type guide 12 as shown on the left part of FIG. 8, the remarks made for a direct contact of the guided wave and the substance to be measured remain valid. The thickness w of the sensitive nonconductor obey the same restraints as for the OIS1 type guide.

b) If the index of the sensitive nonconductor nDS is greater than nSiO2: nDS > nSiO2-HI; it is possible to take here as a reference the index of the SiO2-HI as the largest able to be obtained with usual dopants: boron, phosphorus, nitrogen, germanium or titanium.

Figure 9:
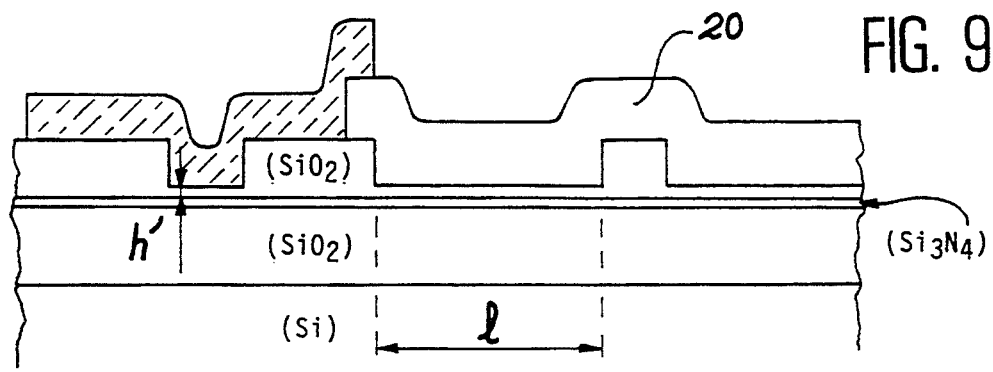

For an OIS1 type guide as shown on the left part of FIG. 9, this measuring guide 12 is embodied by a lateral confinement of light obtained with the aid of the sensitive nonconductor.

Figure 10:
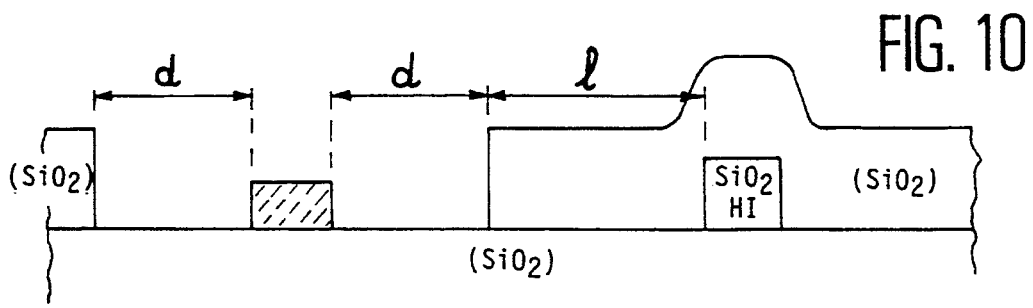

The remaining thickness of the silica SiO2 h' shall be less than p, namely the penetration of the dying out wave of the guided mode.

for a guide 12, the OIS2 structure is unsuitable in this case if it is desired to retain the core of the SiO2-HI microguide. However, it is possible to embody the core of this guide 12 with the sensitive nonconductor if the latter is sufficiently transparent. But this assumes that the technology associated with this sensitive nonconductor is sufficiently developed, which is rarely the case. FIG. 10 shows a representation of two adjacent guides 11 and 12 of the spiral cross section in the case where the sensitive nonconductor is technologically able to be used: for example, etched. The sensitive polymer here plays both the role of the core and that of the sensitive nonconductor.

In the inlet and outlet portions of the spiral 10 outside the spiralled zone, the two measuring and reference guides 11 and 12 respectively retrieve an identical structure of the type of the reference guide (OIS1 ot OIS2). The input and output links of the measuring guide with the central portion of this guide used for measuring may be effected by direct coupling if the structures of the two guides are extremely close to one another (nDS close to the index of the silica) or by adiabatic transitions (if nDS is completely different from nSiO2 in the case where an OIS2 structure is used). These adiabatic transition zones may be embodied as described in the document "Applied Physical Letters" 55 (23) of 4 December 1989, pages 2389–2391 by Y. Shani et. al and entitled "Efficient coupling of a semiconductor laser to an optical fiber by means of a taped waveguide on silicon".

In the case of an indirect contact between the guided wave and the substance to be measured, embodiment variants are shown on FIGS. 11 to 14 relating to OIS1 structures (FIGS. 11 and 13) and OIS2 (FIGS. 12 and 14) respectively for nDS<nSiO2-HI and nDS>nSiO2-HI. These embodiment variants are advantageous in that they are able to improve rendering symmetrical the stacking of films between the reference guide 11 and the measuring guide 12 in cases where a sensitive material is used and are thus able to better suppress any parasitic effects.

On FIGS. 11 to 14, the distance l is calculated so that there is no longer any interaction between the guided light extending under the various guides and the covering media for this distance.

Figure 11:
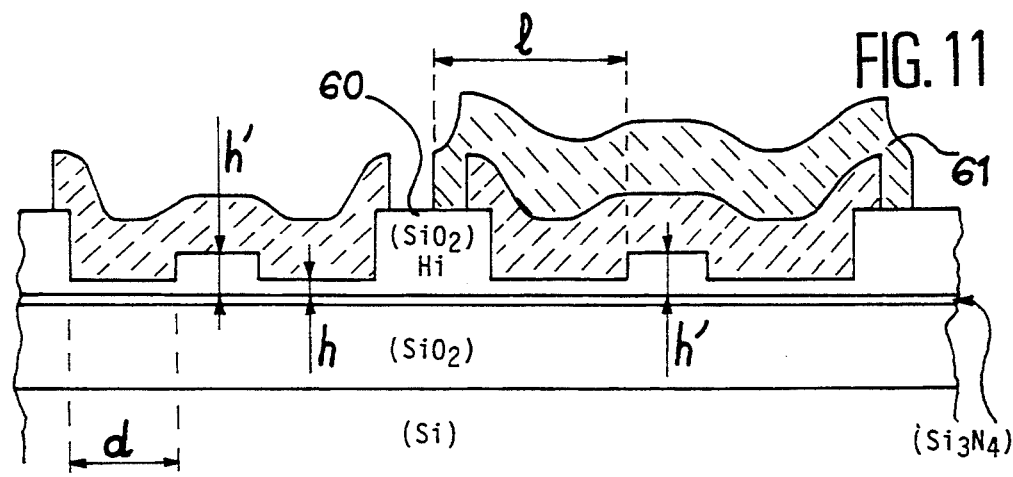
Figure 12:
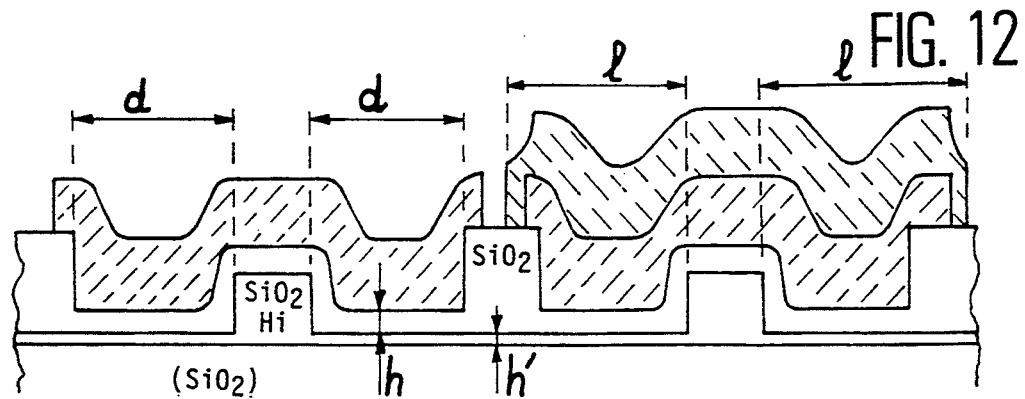
Figure 13:
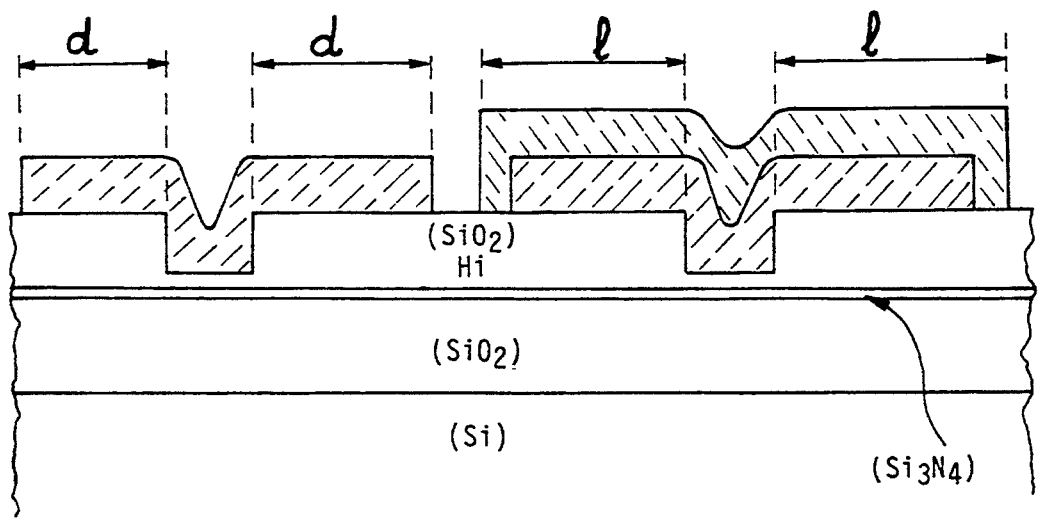
Figure 14:
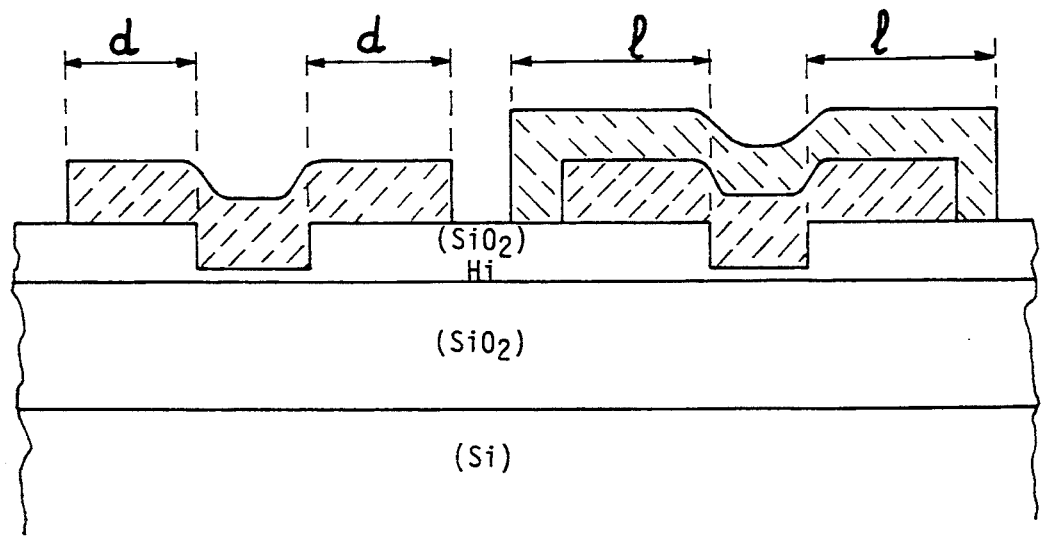

FIGS. 11 and 12 show an SiO2-HI or SiO2 silica block 60 whose width depends on the values selected for d and l and on the distance separating the cores of the guides 11 and 12. The width of this block may be nil.

The protection nonconductor 61 of the guides ought to be able to be placed at a low temperature as it shall cover the sensitive material whose resistance to temperature is frequently low. This certainly constitutes a limitation concerning the range of protective materials which may be used, but there is a wide range of other possibilities: various polymers, SiO2 silica deposit or another substance by means of cathodic spraying or evaporation. However, the optic quality of the protective film is not important.

Of course, the examples given above do not need to be regarded as restrictive concerning the nature of the components of the guided structure and the latter may be virtually formed of all the materials conventionally used in integrated optics and especially glass whose index may be made to vary via the exchange of ions, or semiconductor or lithium niobate structures.

The invention is able to measure the characteristics of gases whose refraction indices are still close to 1 and thus lower than the index of the silica and liquids, provided the index of the liquid nl is such that it does not destroy the confinement of the luminous wave and thus $nL < nSiO2-HI$.

For liquids, measurement generally does not consist of revealing the presence of the liquid in the environment of the sensor (much simpler sensors are then able to be embodied), but the modification of the index of a liquid in which the sensor is immersed, for example the index modification linked to the pH variation (H+ concentration) or to any other extremely low solute concentration quantity.

Figure 15:
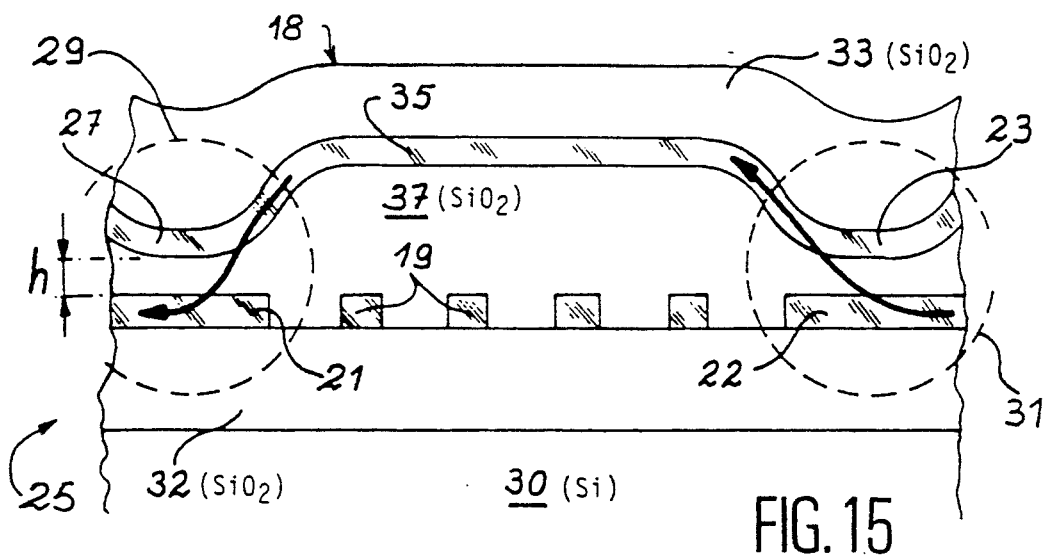
Figure 15A:
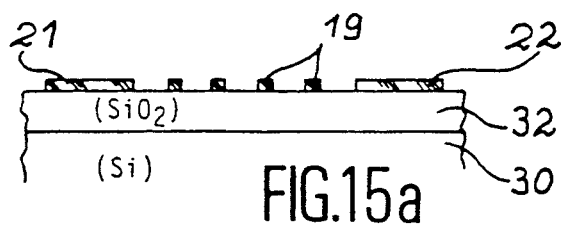
Figure 16:
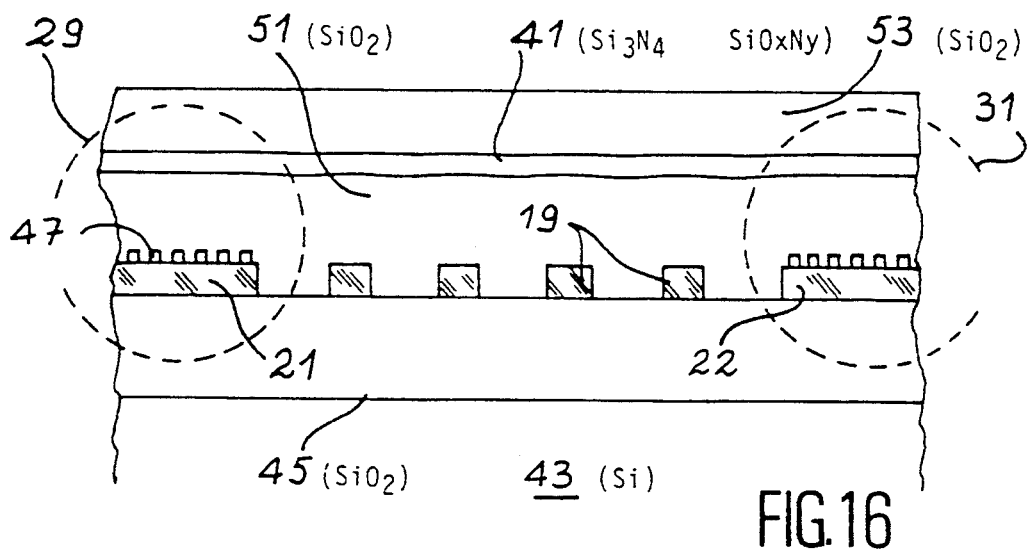

FIGS. 15 and 16 make it possible to describe possible embodiment modes of the passage 18 of FIGS. 1 and 2. In these figures, the passages described are upper crossings in the manner of bridges. But it needs to be clearly understood that this is not restrictive and that solutions which would consist of using lower passages would also be possible.

So as to simplify the description, a single crossing is described hereafter, it being understood that each guide of the spiral is associated with one crossing.

In the case of FIG. 15, two identical guiding structures are superimposed in the passage zone 18 with one disposed above the other so as to embody the desired crossing bridge. The guiding structure used in this described example is an Si/SiO2/SiO2 high index/SiO2 type structure, but could also be a different structure.

In the case of FIG. 15, the basic structure comprises a silicon film 30 surmounted by a silica film 32 and various guide blocks 19 doped with SiO2 silica. Amongst these are the blocks of the guides 11 and 12 of the actual spiral 10 and the two lower blocks 21 and 22 of the couplers 29 and 31 of this first structure with the upper structure which surmounts it. This upper structure comprises a silica film 33 and a doped silica wave guide core 35; as regards the film 37 common to the two structures, this is made of silica. FIG. 15 also shows the coupler 29 constituted by the block 21 and the portion 27 immediately above the core of the guide 35 and the coupler 31 situated on the other edge of the spiral and constituted by the block 22 and the surbased portion 23 of the core of the guide 35. The continuous line arrows symbolize the way in which the light passes in the coupler 31 of the block 22 to the core of the guide 35 and in the coupler 29 of the core of the guide 35 in the block 21. This mode of implementation thus allows for crossing of the zone 18 without adversely affecting the propagation of the light into the guides of the spiral 10.

Figure 15B:
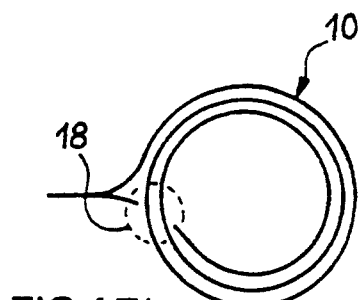

FIGS. 15a to 16g show by way of explanation the main stages of the method for preparing the crossing bridge of FIG. 15. The method starts, as shown on FIG. 15, by placing the blocks 21 and 22 of the intended couplers and the blocks of the spiral guides 19 of the spiral 10 on a silicon substrate coated with silica. At this stage, the system appears as seen from the top on FIG. 15b.

Figure 15C:
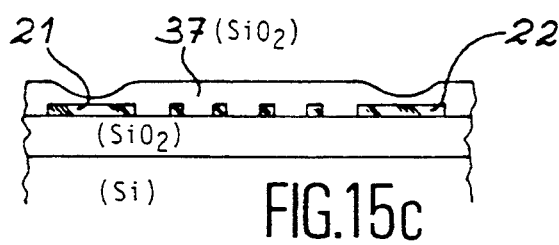
Figure 15D:
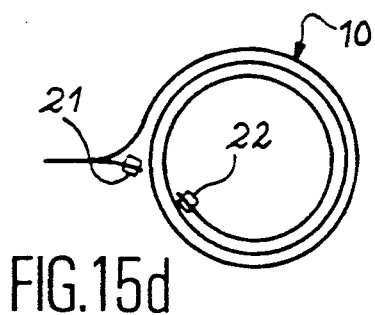

The next stage (FIG. 15c) consists of depositing the intermediate film of silica 37 by means of a plasma-assisted vapor phase chemical deposit followed by a chemical etching. Above the blocks 21 and 22, this film comprises scallopings in which the light pipe 35 is to be subsequently housed. The top view corresponding to the state of this FIG. 15 is represented on FIG. 15d.

Figure 15E:
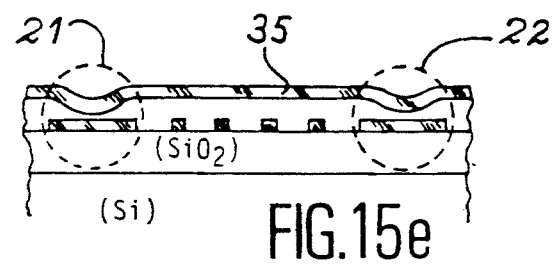
Figure 15F:
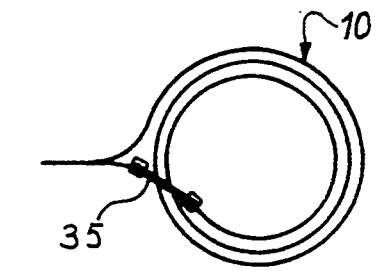

The next phase (FIG. 15e) consists of depositing on the preceding structure the core of the guide structure 35 and of etching this core through a mask (for ensuring the lateral confinement of the light). The material of the core 35 is doped silica. The top view of the same device in this state is represented by FIG. 15f.

Figure 15G:
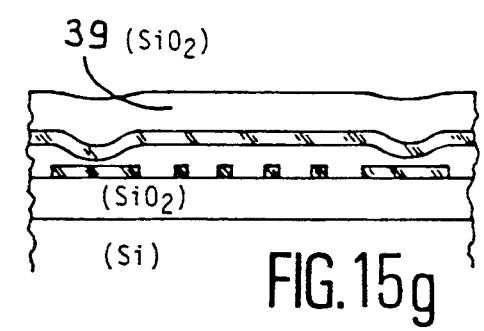

The next stage consists in depositing the final film or superstrate 39 as shown on FIG. 15g. This deposit of silica SiO2 may also be embodied by means of a plasma-assisted vapor phase chemical depositing.

As experts in this field are aware, the given thicknesses of the various films depend on the desired effective indices for each of the latter and on the need to obtain a correct passage of the dying out wave at the level of the couplers 29 and 31.

With reference now to FIG. 16, there follows a description of another embodiment of the crossing zone where this zone is obtained with the aid of two non-identical superimposed structures. In a case of this type, the coupling between the lower structure and the upper structure is generally extremely slight as the speeds of the guided luminous waves in each structure are different. So that the passage of light nevertheless takes place between these two structures, it is necessary to establish the couplers of a network with a pitch p so that:

$$\beta 1 + 2\pi m/p = \beta 2$$

with $$\beta 1 = (2\pi n1)/\lambda o \text{ and } \beta 2 = (2\pi n2)/\lambda o$$

$\beta 1$ and $\beta 2$ being the propagation constants of the modes of the structures of the upper and lower guides, p the pitch of the network, m the refraction sequence and n1 and n2 the effective indices of the cores 19 and 41 of the upper and lower guides. If account is taken of the preceding conditions, the coupling between the upper and lower structures is perfect and allows for the embodiment of the crossing on the zone 25. In the example of FIG. 16, the lower structure is of the doped/SiO2/Si/SiO2/-SiO2 type and that of the upper guide is of the Si/SiO2/Si3N4 (or SiOxNy)/SiO2 type. This is what appears on FIG. 16 where the lower substrate 43 is a silicon substrate and surmounted by a first silica film 45. Situated on the surface of this film 45 are the guide blocks of the doped silica spiral 10, as well as the support blocks 21 and 22, also doped with silica, of the networks 47 and 49.

The silica film 51 surmounting the blocks of the guides 19 and the blocks 21 and 22 of the couplers 29 and 31 is common to the lower and upper structures. The upper structure includes the core of the actual guide 41 made of silicon nitride Si3N4 or an SiOxNy type compound and is surmounted by the silica film 53. The networks 47 and 49 ensure luminous coupling between the two preceding structures. The structure of FIG. 16 is technologically viable if for the constants $\beta 1$ and $\beta 2$ the previously mentioned conditions are observed, that is more particularly if the thicknesses and indices of the various guides are suitable and coherent with the pitch p of the networks 47 and 49.

Although experts in this field know how to embody the guiding structures of FIG. 16, FIGS. 16a to 16f diagrammatically show the main stages for embodying this structure.

Figure 16A:
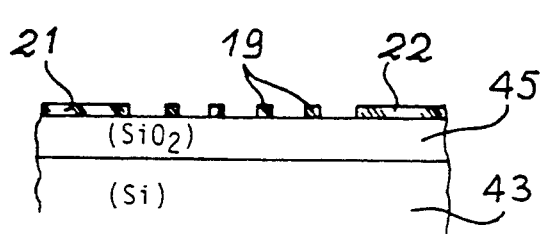
Figure 16B:
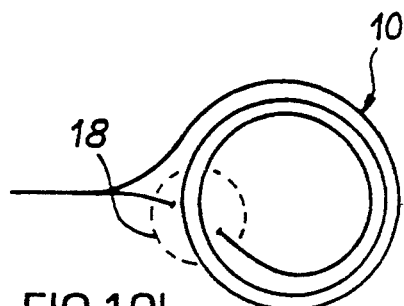
Figure 16C:
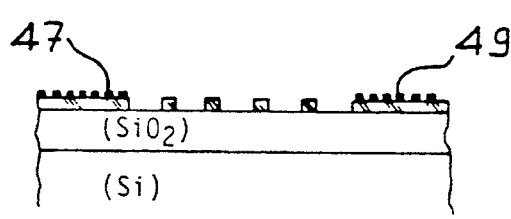

FIG. 16a shows the silicon substrate 43 surmounted by the silica film 45 on which the blocks 19, 21 and 22 are etched by conventional means. The structure reached at this stage is shown at the top part of FIG. 16b.

Figure 16D:
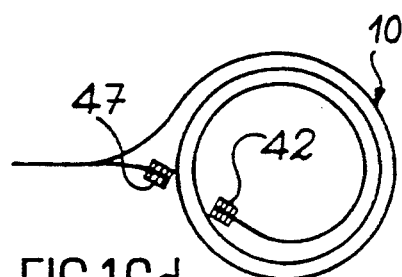

The next stage consists of embodying the networks 47 and 49 by means of depositing and then etching through a mask a nonconducting film with an index differing from that of the film 51. FIG. 16d shows the state of this same structure viewed from the top with the networks 47 and 49 situated on both sides of the pipes of the spiral 10.

Figure 16E:
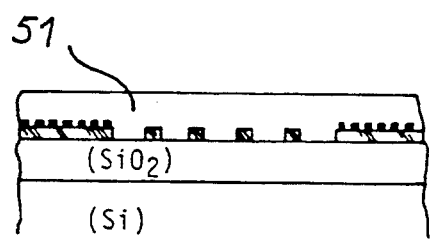
Figure 16F:
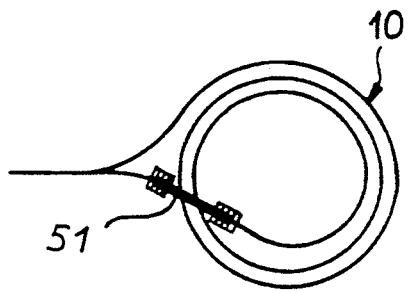

FIG. 16e shows the depositing by vapor phase chemical means of the intermediate silica film 51 common to the two structures. The state of the device is then visible from the top on FIG. 16f; it merely suffices to complete it by depositing the core 41 of the guides followed by an etching and a depositing of the silica substrate SiO2. As in the example of FIG. 15, the thicknesses of each of the deposits are selected by an expert in this field according to the effective desired indices for each film.

The sensor of the invention as described above is able to be generally applied for chemical measurements:
 detection of gases,
 liquid concentration measurement (pH, solute concentration, etc).
 measuring the concentration of antigens after antibody transplanting or grafting by means of a sensitive nonconductor: the only difference is that in this case, the thickness of the sensitive nonconductor is very small (several tens of nm). The transplanting principle is well known, especially as regards silica.

What is claimed is:

1. Sensor with integrated optics to detect chemical substances, which includes a double spiral interlaced with two wave guides and integrated on a substrate wherein a first of the two wave guides is a reference guide isolated from the influence of the substance to be measured, a second wave guide being a measuring guide affected by the substance to be measured, said sensor receives a signal from a light source through a first optical component enabling the light intensity emitted by the source to be separated into two portions and sends outgoing signals onto at least one detector through a second optical component.

2. Sensor according to claim 1, wherein the spiral comprises inlets and outlets, and wherein the inlets and outlets of the spiral are situated on the same side of the substrate.

3. Sensor according to claim 1, wherein the second wave guide is affected by the substance to be measured either directly or by means of a relay material.

4. Sensor according to claim 1, which detects luminous intensities at the outlets of the two guides.

5. Sensor according to claim 1, which measures phase variations produced between the first wave guide and the second wave guide.

6. Sensor according to claim 5, wherein the second optical component is a bicoupler.

7. Sensor according to claim 1, wherein the second optical component is able to connect the two wave guides and two detectors for detecting the luminous intensities at the outlet of said guides.

8. Sensor according to claim 1, wherein in the inlet and outlet portions of the double spiral, the two wave guides have a structure identical to that of the first wave guide.

9. Sensor according to claim 8, wherein outside the inlet and outlet portions of the spiral, the second wave guide has a central measuring portion which has a different structure allowing for measurement, the links between the inlet and outlet portions of the second wave guide and the central measuring portion being effected by an adiabatic transition.

10. Sensor according to claim 1, wherein the guides of the spiral are crossed by one of the two extremities of said guides, the crossing being embodied via the direct crossing of the guides within a plane of the spiral itself, with crossing angles of said guides preferably being greater than 10 degrees.

11. Sensor according to claim 1, wherein the crossing of spires of the spiral by one of the two extremities of the two guides of the spiral is embodied in the form of one upper (or lower) passage in the manner of a bridge by superimposing two crossed guiding structures, the lower structure constituted by the spiral itself being coupled optically to the upper crossing structure by means of two couplers situated on the incoming (or outgoing) extremity respectively on both sides of the wave guides of the spiral.

12. Sensor according to claim 5, wherein the second optical component is a tricoupler able to interfere with the outgoing signals of the guides so as to measure the phase variations induced between the first wave guide and the second wave guide.

13. Sensor according to claim 12, wherein the second optical component includes a central guide associated with the reference and measuring guides and disposed between the guides.

14. Sensor according to any one of the preceding claims, wherein the luminous wave guides are embodied in one of the $Si/SiO_2/Si_3N_4/SiO_2$ (OIS1) and $Si/SiO_2/SiO_2$ high index/$SiO_2$ (OIS2) structures.

* * * * *

UNITED STATES PATENT AND TRADEMARK OFFICE
CERTIFICATE OF CORRECTION

PATENT NO. : 5,394,239
DATED : February 28, 1995
INVENTOR(S) : Serge Valette

It is certified that error appears in the above-indentified patent and that said Letters Patent is hereby corrected as shown below:

In the title, delete "SPINAL" and insert --"SPIRAL".

Column 8, line 31, delete "nl" and insert --nL--.

Signed and Sealed this

Thirteenth Day of June, 1995

Attest:

BRUCE LEHMAN

*Attesting Officer*   *Commissioner of Patents and Trademarks*